US012811013B2

(12) United States Patent
Pearsall

(10) Patent No.: US 12,811,013 B2

(45) Date of Patent: Nov. 24, 2026

(54) ERGONOMIC ASSESSMENT TOOL

(71) Applicant: THE BOEING COMPANY, Arlington, VA (US)

(72) Inventor: Nik J. Pearsall, Brisbane (AU)

(73) Assignee: The Boeing Company, Arlington, VA (US)

( * ) Notice: Subject to any disclaimer, the term of this patent is extended or adjusted under 35 U.S.C. 154(b) by 85 days.

(21) Appl. No.: 18/539,200

(22) Filed: Dec. 13, 2023

(65) Prior Publication Data

US 2025/0201418 A1 Jun. 19, 2025

(51) Int. Cl.

| | |
|---|---|
| ***G16H 50/30*** | (2018.01) |
| ***A61B 5/00*** | (2006.01) |
| ***G06F 30/17*** | (2020.01) |
| ***G06Q 10/0635*** | (2023.01) |
| ***G06T 7/20*** | (2017.01) |

(52) U.S. Cl.

CPC ........... *G16H 50/30* (2018.01); *A61B 5/4561* (2013.01); *G06F 30/17* (2020.01); *G06Q 10/0635* (2013.01); *G06T 7/20* (2013.01)

(58) Field of Classification Search

CPC ....... G16H 50/30; G06F 30/17; A61B 5/4561; G06Q 10/0635; G06T 7/20

See application file for complete search history.

(56) References Cited

U.S. PATENT DOCUMENTS

| | | | | |
|---|---|---|---|---|
| 8,005,656 B1 * | 8/2011 | Ankory | G06Q 10/04 | 702/182 |
| 10,762,459 B2 * | 9/2020 | Garnavi | G06Q 10/0635 | |
| 10,762,460 B2 * | 9/2020 | Garnavi | G09B 29/007 | |
| 11,769,110 B1 * | 9/2023 | Bourke | G06Q 10/0631 | 705/28 |
| 2003/0066026 A1 * | 4/2003 | Jaffe | G06F 17/10 | 715/200 |

(Continued)

FOREIGN PATENT DOCUMENTS

| | | | | |
|---|---|---|---|---|
| KR | 102295699 B1 * | 8/2021 | G06T 13/40 | |
| WO | WO-2022030696 A1 * | 2/2022 | A63B 21/0626 | |

OTHER PUBLICATIONS

Risvas et al., "Biophysics-based simulation of virtual human model interactions in 3D virtual scenes," 2020 IEEE Conference on Virtual Reality and 3D User Interfaces Abstracts and Workshops (VRW); DOI 10.1109/VRW50115.2020.00026. (Year: 2020).*

(Continued)

*Primary Examiner* — Jonathon A. Szumny

(74) *Attorney, Agent, or Firm* — Massey Bean & Lewis

(57) ABSTRACT

The present disclosure provides an ergonomic assessment tool and techniques for performing an economic assessment of a workspace. In one aspect, an ergonomic assessment tool can include a computing system configured to perform an operation, the operation includes inputting a 3D model of a workspace into a 3D environment of an ergonomic assessment tool; simulating, in the 3D environment, a user interacting with the workspace; assessing, during the simulating, one or more physiological angles of the user as the user interacts with the workspace in the 3D environment; identifying a potential ergonomic risk by comparing the one or more physiological angles relative to an anthropometric standard; and causing, when identified, the potential ergonomic risk to be presented.

19 Claims, 6 Drawing Sheets

(56) References Cited

U.S. PATENT DOCUMENTS

| | | | | |
|---|---|---|---|---|
| 2006/0166737 | A1* | 7/2006 | Bentley | A63B 69/36 463/43 |
| 2008/0186189 | A1* | 8/2008 | Azzaro | G16H 50/20 340/573.7 |
| 2009/0046056 | A1* | 2/2009 | Rosenberg | G06F 3/011 345/156 |
| 2009/0326553 | A1* | 12/2009 | Mustufa | A61B 34/74 606/130 |
| 2013/0332128 | A1* | 12/2013 | Miles | G16H 50/50 703/6 |
| 2015/0019135 | A1* | 1/2015 | Kacyvenski | G01P 7/00 702/19 |
| 2017/0235853 | A1* | 8/2017 | Griswold | G06F 30/20 703/1 |
| 2017/0245806 | A1* | 8/2017 | Elhawary | A61B 5/1122 |
| 2019/0290198 | A1* | 9/2019 | Belson | A61B 5/4878 |
| 2019/0311812 | A1* | 10/2019 | Sweeney | A61B 5/02 |
| 2019/0329043 | A1* | 10/2019 | Sharma | A61N 1/37252 |
| 2021/0059616 | A1* | 3/2021 | Abrol | A61B 5/7435 |
| 2022/0006813 | A1* | 1/2022 | Jorasch | G16H 50/30 |
| 2022/0304594 | A1* | 9/2022 | Rehbein | A61B 5/1121 |
| 2023/0177228 | A1* | 6/2023 | Bourret | G06F 30/17 703/7 |
| 2023/0177437 | A1* | 6/2023 | Bourret | G06Q 10/06398 705/7.28 |
| 2024/0172963 | A1* | 5/2024 | Carbo, Jr. | A61B 5/01 |
| 2024/0202463 | A1* | 6/2024 | Mazareinezhad | G06F 11/3612 |
| 2024/0212287 | A1* | 6/2024 | Xi | G06V 40/103 |

OTHER PUBLICATIONS

Makarova et al., Creating a Safe Working Environment Via Analyzing the Ergonomic Parameters of Workplaces on an Assembly Conveyor, presented at the 6th IESM Conference, Oct. 2015, Seville, Spain. (Year: 2015).*

Grobelny et al., "Preventing Work-Related Musculoskeletal Disorders in Manufacturing by Digital Human Modeling," Int. J. Environ. Res. Public Health 2020, 17, 8676; doi: 10.3390/ijerph17228676. (Year: 2020).*

Aaltonen, I., & Laarni, J. (2017). Field evaluation of a wearable multimodal soldier navigation system. Applied Ergonomics, 63, 79-90. doi:10.1016/j.apergo.2017.04.005.

Bittner, A.C. (1987). CADRE: A Family of Manikins for Workstation Design, Trends in Ergonomics/Human Factors IV, Pub: Elsevier, pp. 733-740.

HFES 300 Committee (2004). Guidelines for Using Anthropometric Data in Product Design. The Human Factors & Ergonomics Society.

Kroemer (2006). Extra-Ordinary Ergonomics—How to accommodate small and big persons, the disabled and elderly, expectant mothers, and children. CRC Press.

Grabowski, M., Rowen, A., & Rancy, J.P. (2018). Evaluation of wearable immersive augmented reality technology in safety-critical systems. Safety Science, 103, 23-32. doi: 10.1016/j.ssci.2017.11.013.

Rui, L., Chuan, L., Yingzhi, D., & Dong, Z. (2009). The preliminary study on the human-factor evaluation system for maintainability design. International Conference on Intelligent Human-Machine Systems and Cybernetics. DOI 10.1109/IHMSC.2009.152.

Stanton, N. A., Salmon, P. M., Rafferty, L. A., Walker, G. H., Baber, C., & Jenkins, D. P. (2017). Human factors methods: a practical guide for engineering and design. CRC Press.

* cited by examiner

ERGONOMIC ASSESSMENT TOOL

FIELD

Aspects of the present disclosure relate to an ergonomic assessment tool.

BACKGROUND

Pain, fatigue, and injuries to the musculoskeletal system may result from sustained inadequate working postures that are often caused by poor work conditions. Musculoskeletal pain and fatigue frequently influence posture control, which can increase the risk of errors and may result in reduced quality of work or production, particularly in hazardous situations. Ergonomically-friendly designs help to avoid these adverse effects.

SUMMARY

The present disclosure provides a method in one aspect, the method includes inputting a 3D model of a workspace into a 3D environment of an ergonomic assessment tool; simulating, in the 3D environment, a user interacting with the workspace; assessing, during the simulating, one or more physiological angles of the user as the user interacts with the workspace in the 3D environment; identifying a potential ergonomic risk by comparing the one or more physiological angles relative to an anthropometric standard; and presenting, when identified, the potential ergonomic risk.

In one aspect, in combination with any example method above or below, the method includes applying, during the simulating, a gravity modifier so as to simulate gravity on the user in the 3D environment.

In one aspect, in combination with any example method above or below, presenting the potential ergonomic risk comprises presenting, on a display in real time, a visual cue indicating that a first physiological angle of the one or more physiological angles is not within an acceptable range of the anthropometric standard.

In one aspect, in combination with any example method above or below, the visual cue indicating that the first physiological angle is not within the acceptable range of the anthropometric standard is presented as a color indicator positioned adjacent the first physiological angle of the user on the display, and wherein the color indicator changes from a first color to a second color when the first physiological angle is not within the acceptable range of the anthropometric standard.

In one aspect, in combination with any example method above or below, the method includes presenting, on a display during the simulating, the one or more physiological angles, the one or more physiological angles are presented adjacent respective joints of the user.

In one aspect, in combination with any example method above or below, the one or more physiological angles dynamically update on the display as the user moves through a range of motion.

In one aspect, in combination with any example method above or below, the one or more physiological angles correspond to joint angles, posture angles, or both, of the user.

In one aspect, in combination with any example method above or below, the anthropometric standard is adjustable in real time during the simulating.

In one aspect, in combination with any example method above or below, presenting the potential ergonomic risk comprises exporting an ergonomic data sheet that corresponds the one or more physiological angles relative to the anthropometric standard through a range of motion of the user.

In one aspect, in combination with any example method above or below, the ergonomic data sheet is exported to an ergonomic report generator that generates an ergonomic report that indicates the potential ergonomic risk to the user as a number of instances per unit of time that at least one of the one or more first physiological angles of the one or more physiological angles is not within an acceptable range of the anthropometric standard.

In one aspect, in combination with any example method above or below, the ergonomic data sheet is exported to an ergonomic report generator that generates an ergonomic report that indicates the potential ergonomic risk to the user as a percentage of time during the simulating that at least one of the one or more first physiological angles of the one or more physiological angles is not within an acceptable range of the anthropometric standard.

In one aspect, in combination with any example method above or below, the method includes acquiring motion data from an actual user performing an actual range of motion, and wherein a range of motion that the user performs to interact with the workspace in the 3D environment mimics the actual range of motion.

In one aspect, in combination with any example method above or below, the workspace is modifiable in real time during the simulating.

In one aspect, in combination with any example method above or below, the method includes generating a workspace change recommendation for the workspace based at least in part on the potential ergonomic risk that is identified.

The present disclosure also provides an ergonomic assessment tool. The ergonomic assessment tool includes one or more processors and one or more memory devices storing a program, which, when executed by any combination of the one or more processors, causes the one or more processors to perform an operation. The operation includes inputting a 3D model of a workspace into a 3D environment of an ergonomic assessment tool; simulating, in the 3D environment, a user interacting with the workspace; assessing, during the simulating, one or more physiological angles of the user as the user interacts with the workspace in the 3D environment; identifying a potential ergonomic risk by comparing the one or more physiological angles relative to an anthropometric standard; and causing, when identified, the potential ergonomic risk to be presented.

In one aspect, in combination with any example ergonomic assessment tool above or below, the operation further includes applying, during the simulating, a gravity modifier so as to simulate gravity on the user in the 3D environment.

In one aspect, in combination with any example ergonomic assessment tool above or below, in causing the potential ergonomic risk to be presented, when identified, the operation includes presenting, on a display in real time, a visual cue indicating that a first physiological angle of the one or more physiological angles is not within an acceptable range of the anthropometric standard.

In one aspect, in combination with any example ergonomic assessment tool above or below, the operation further includes presenting, on a display during the simulating, the one or more physiological angles, the one or more physiological angles are presented adjacent respective joints of the user, and wherein the one or more physiological angles dynamically update on the display as the user moves through a range of motion.

In one aspect, in combination with any example ergonomic assessment tool above or below, the workspace is modifiable in real time during the simulating.

The present disclosure also provides a non-transitory, computer readable medium. The non-transitory, computer readable medium includes instructions that, when executed by one or more processors, cause the one or more processors to perform an operation. The operation includes inputting a 3D model of a workspace into a 3D environment of an ergonomic assessment tool; simulating, in the 3D environment, a user interacting with the workspace; assessing, during the simulating, one or more physiological angles of the user as the user interacts with the workspace in the 3D environment; identifying a potential ergonomic risk by comparing the one or more physiological angles relative to an anthropometric standard; and causing, when identified, the potential ergonomic risk to be presented.

BRIEF DESCRIPTION OF THE DRAWINGS

So that the manner in which the above recited features can be understood in detail, a more particular description, briefly summarized above, may be had by reference to example aspects, some of which are illustrated in the appended drawings.

DETAILED DESCRIPTION

Figure 1:
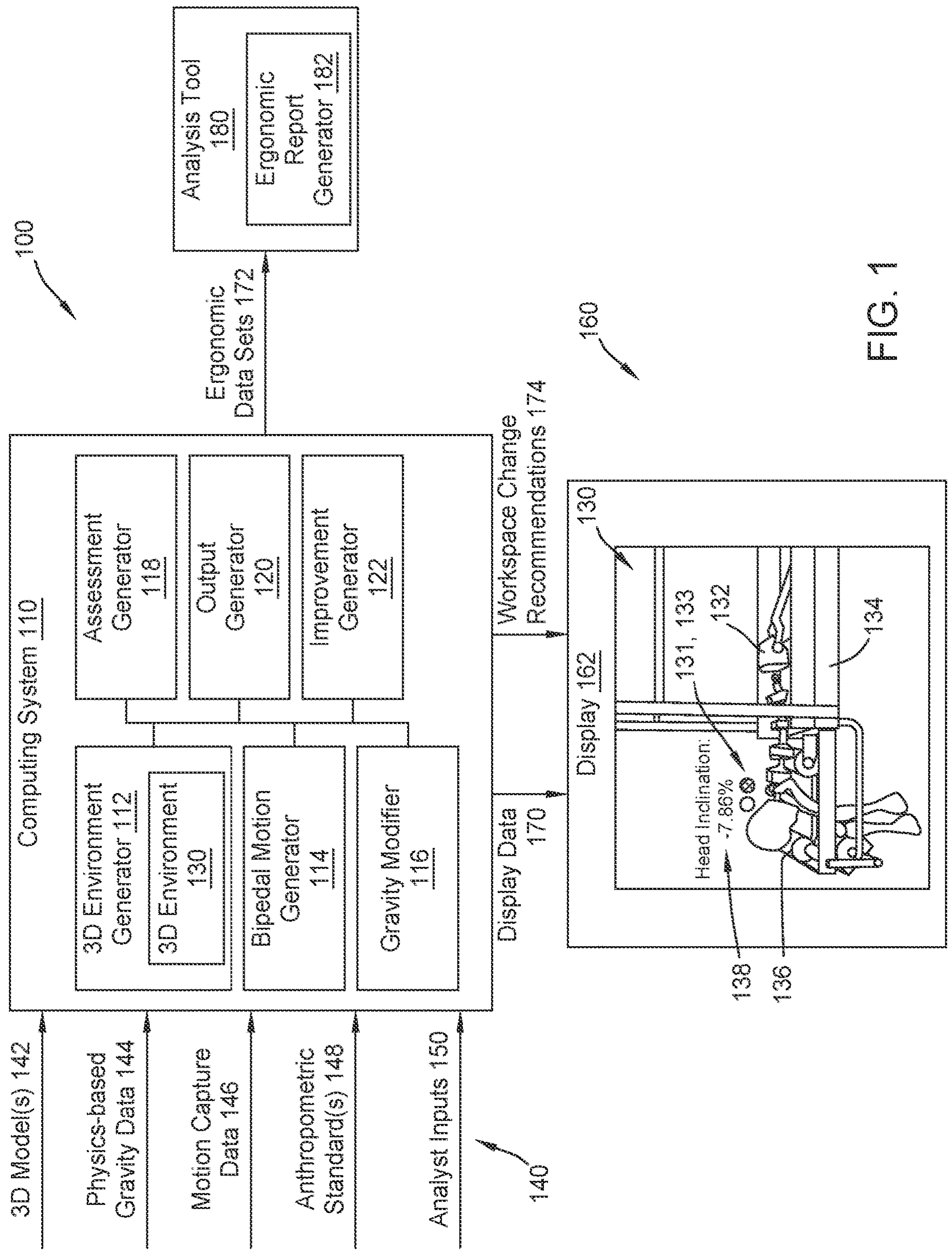
FIG. 1 is system diagram of an ergonomic assessment tool according to aspects of the present disclosure.

Analysis of a physical working environment is currently performed by practitioners using a number of Human Factors Engineering (HFE) techniques.

Assessment of physical aspects of a particular design and how it will accommodate the range of body shapes found within the intended user population are considered. HFE practitioners aim to assess a design as early as practicable to ensure that the design allows the user to perform their tasks safely and efficiently. Currently, the tools available to assess these human factors allow this early assessment to occur only within a 2D representation or in 3D where true body motion is not represented, nor are the angles of joints communicated or easily assessed. When assessing design suitability for physical human factors using such conventional tools, there is opportunity for error or limited ability for consideration of the operational context.

For example, anthropometric measures are typically obtained to justify design suitability for physical human factors, such as posture. But, such anthropometric measures are generally based on static measurements, which do not capture the natural movements of work as done. Moreover, conventional tools do not consider how the forces of gravity pull on the human body. Placing a static manikin in a 2D Design may not adequately capture the dynamics of the human body under the effects of the natural environment. In addition, placing a ridged manikin within a simulated environment may not truly represent the human body when placed under the natural forces of gravity.

Moreover, in some instances, designs may need to meet more than one human factors design standard for an intended user population. For instance, a design may need to meet both a military and a civilian human factors design standard. Conventional ergonomic assessment tools do not provide a means to ensure design suitability for physical human factors for multiple human factors design standards.

The present disclosure provides an ergonomic assessment tool that addresses one or more of the above-noted challenges. The ergonomic assessment tool of the present disclosure can function to determine acceptable limits of static and dynamic working postures in accordance with accepted physical ergonomic practice. The ergonomic assessment tool can also be used to identify physical ergonomic risks, e.g., during an early design stage of a product development process. Specifically, the ergonomic assessment tool of the present disclosure can provide an HFE practitioner with a range of automatically generated physical ergonomic data sets and visual cues, based on one or more predefined physical ergonomic standards, to be utilized for overall design assessment. The ergonomic assessment tool can simulate the dynamics of the human body under the effects of the natural environment, including the effects of gravity on the human body, and can provide visual cues communicating relevant ergonomic data, such as the angles of joints. In addition, the ergonomic assessment tool can allow for real-time modifications to the design in view of the assessed human factors of the design.

The ergonomic assessment tool of the present disclosure can provide certain advantages, benefits, and/or technical effects, including, without limitation, faster and more accurate and efficient design analysis; easier and more efficient physical ergonomic assessments; training to use the ergonomic assessment tool is easier than training in physical ergonomic standards and measurements as dynamic visual cues are presented; safer human-centered design and outcomes; and reduction in rework and error remediation later in the design process.

FIG. 1 is system diagram of an ergonomic assessment tool 100. The ergonomic assessment tool 100 functions generally to assess whether a workspace is ergonomically acceptable relative to an anthropometric standard and can present real time information regarding one or more physiological angles of a user as the user interacts with the workspace in a 3D environment. In this way, potential ergonomic risks can be identified and presented to an analyst in real time. Moreover, in some aspects, the ergonomic assessment tool 100 can allow for real-time modifications to the workspace. The ergonomic assessment tool 100 is particularly useful for workspace assessments at an early stage of a design process. The ergonomic assessment tool 100 is adaptable to assess human factors for many different types of workspaces or designs.

As depicted in FIG. 1, among other things, the ergonomic assessment tool 100 can include a computing system 110 and one or more output devices 160, such as a display 162 communicatively coupled with the computing system 110. The output devices 160 can also include speakers, printers, touchscreens, a combination thereof, etc. that can present information to a user. The computing system 110 can include one or more processors and one or more non-transitory memory devices. The memory devices can store a program, which, when executed on any combination of the one or more processors, can cause the one or more processors to perform an operation, such the operation disclosed herein.

The architecture of the computing system 110 is further described with reference to FIG. 7.

The computing system 110 can receive a number of inputs 140, including, without limitation, one or more 3D models 142, physics-based gravity data 144, motion capture data 146, one or more anthropometric standards 148, and one or more analyst inputs 150. These inputs can be used by the computing system 110 to execute an ergonomic assessment. The 3D models 142 (e.g., 3D CAD models) can each be 3D digital representations of a workspace or design. The physics-based gravity data 144 can include data, e.g., in the form of scripts, that can be executed by the computing system 110 to simulate the effects of gravity on a user. The physics-based gravity data 144 can include data sets for a plurality of different conditions, such as gravity data for conditions near the equator, far from the equator, at low altitude, at high altitude, etc. The motion capture data 146 can include data representative of an actual user performing a motion in a real environment. The motion can be intended to mimic the motion that the user is to undertake during a simulation. For instance, an actual user can wear sensors while performing a predefined task. The sensors can capture the motion data. The motion data can then be used as a baseline to move a user within a 3D environment. The one or more anthropometric standards 148 can include, without limitation, civilian standards, military standards, a first country standard, a second country standard, etc. that define the acceptable limits of static and dynamic working postures of users in accordance with accepted physical ergonomic practice. Analyst inputs 150 can be input into the computing system 110, e.g., via one or more input devices, including, without limitation, keyboards, mouse inputs, voice commands, motion commands, a combination thereof, etc. Such analyst inputs 150 can be used to control a simulation, such as by placing a user or simulated human bipedal in different positions within a workspace.

One or more of the 3D models 142 can be input into a 3D environment 130 and assessed, analyzed, and/or otherwise considered for ergonomic compliance or potential ergonomic risk. The 3D environment 130 can be generated by a 3D environment generator 112 or engine of the computing system 110. The 3D environment generator 112 can be executed to simulate, in the 3D environment 130, a user interacting with a workspace through a range of motion. The computing system 110 can include a bipedal motion generator 114 that moves a user through a range of motion within the 3D environment in interaction with the workspace. The bipedal motion generator 114 can utilize the motion capture data 146 input into the computing system 110 to mimic the motion of the user within the 3D environment 130 according to the movements of the actual user in a real environment or can be used to simulate a range of motion without the motion capture data 146. For instance, a user within the 3D environment 130 can be moved about the 3D environment 130 via an analyst input 150, and the bipedal motion generator 114 can track and/or record the movements of the user within the 3D environment 130. In this way, motion of a user within the 3D environment 130 can be learned. This motion can then be repeated over a period of time for an ergonomic assessment.

During a simulation, a gravity modifier 116 can be applied on the user interacting with the workspace through the range of motion so as to simulate gravity on the user in the 3D environment 130 that the user would experience in a real environment. The gravity modifier 116 can utilize the physics-based gravity data 144 to impart the proper gravitational forces on the user within the 3D environment 130. The gravitational forces applied to a user can be selectable, e.g. by way of an analyst input 150. Advantageously, by applying the gravity modifier 116, the force on the body from gravity can be simulated. Specifically, by applying gravity to the user within the 3D environment 130, the dynamics of the human body under the effects of gravity can be captured, which can provide for enhanced accuracy with respect to ergonomic assessments.

Further, during a simulation, one or more physiological angles of the user (e.g., one or more joint angles) can be assessed as the user interacts with the workspace through the range of motion in the 3D environment 130. For instance, an assessment generator 118 can be executed to compare the one or more physiological angles of the user to an anthropometric standard, such as a military standard or civilian standard, or both. Based on the comparison, it can be determined whether the workspace is acceptable from an ergonomic standpoint. Specifically, the computing system 110 can identify one or more potential ergonomic risks associated with the workspace by comparing the one or more physiological angles relative to the anthropometric standard. If a given physiological angle reaches a limit corresponding to the given physiological angle, a potential ergonomic risk associated with the given physiological angle can be identified. When no potential ergonomic risks are identified, the workspace can be validated or identified as an ergonomically acceptable workspace or design. In some aspects, the anthropometric standard 148 can be adjusted in real time during the simulation, e.g., between a first standard and a second standard that is different than the first standard. For instance, an analyst can select the first standard and can compare the one or more physiological angles relative to the first standard to identify potential ergonomic risks associated with the first standard. Then, the analyst can select the second standard and can compare the one or more physiological angles relative to the second standard to identify potential ergonomic risks associated with the second standard. This flexibility can be useful to ensure a workspace meets multiple standards, which is particularly useful when a workspace is intended for multiuse or in multiple countries that may have different standards.

The computing system 110 can include an output generator 120 that monitors the simulation and organizes data associated with the simulation into a format that can be output to one or more of the output devices 160. The computing system 110 can output a number of different types of outputs. For instance, the computing system 110 can output display data 170 to the display 162 so that the display 162 can render the 3D environment 130 (with the user 132 interacting with the workspace 134). The computing system 110 can also ouput visual cues, aural cues, haptic feedback, reports, data for reports to be generated by an associated application, workspace/design recommendations, a combination of the foregoing, etc.

For example, the computing system 110 can output a rendering of the 3D environment 130, e.g., on the display 162 as shown in FIG. 1. The rendering can show a user performing one or more actions or interacting with the workspace, e.g., while in a static position or dynamically through a range of motion. For instance, on the display 162 in FIG. 1, a user 132 is shown interacting with a workspace 134 in the 3D environment 130. The user 132 is lying down with her head resting on a headrest 136 and arms dangling through an access opening. In this positon, the user 132 can perform tasks on items below. In view of the design of the workspace 134 and with gravity applied to the user 132, the user's head is at in inclination relative to her spine as shown in the rendered image on the display 162 in FIG. 1.

In some aspects, one or more physiological angles 138 can be calculated and presented on the display 162 during the simulation. The physiological angles can correspond to joint angles, posture angles, or both, of the user 132 and can be presented adjacent their respective joints or posture joints of the user 132 on the display 162. The one or more physiological angles can be "live angle readings" that dynamically update as the user 132 moves through a range of motion within the 3D environment 130. Moreover, the simulation can be paused or moved in slow motion to reveal the physiological angles 138 at a standstill or slower rate than normal speed.

For example, the depicted physiological angle 138 shown in FIG. 1 is a joint angle of the neck of the user 132. As illustrated, the joint angle is depicted adjacent to the neck of the user 132 so that an analyst can readily appreciate the inclination of the neck of the user 132 in her position on the workspace 134. In this example, with the user's head resting on the headrest 136 and gravity applied, the joint angle is depicted as a head inclination of −7.86%.

Notably, one or more potential ergonomic risks can be presented on the display 162 in real time during the simulation. As depicted in FIG. 1, a visual cue 131 is presented on the display 162. The visual cue 131 indicates whether the joint angle is within an acceptable range of the anthropometric standard 148. Particularly, for this example, the visual cue 131 indicating whether the joint angle is within the acceptable range of the anthropometric standard 148 is presented as a color indicator 133 positioned adjacent to the joint angle of the user 132 on the display 162. The color indicator 133 can change from a first color (e.g., green) to a second color (e.g., red) when the joint angle is not within the acceptable range of the anthropometric standard, or specifically a neck inclination angle of the anthropometric standard in this example. Here, a head inclination of −7.86% is not within an acceptable range according to the anthropometric standard, and consequently, the color indicator 133 is the second color (e.g., red), as indicated by the circle containing the cross-hatching. Such a visual cue can make the potential ergonomic risk readily apparent to an analyst. When a joint angle returns or is within an acceptable range of the anthropometric standard, the color indicator 133 can revert to the first color (e.g., green).

Figure 2:
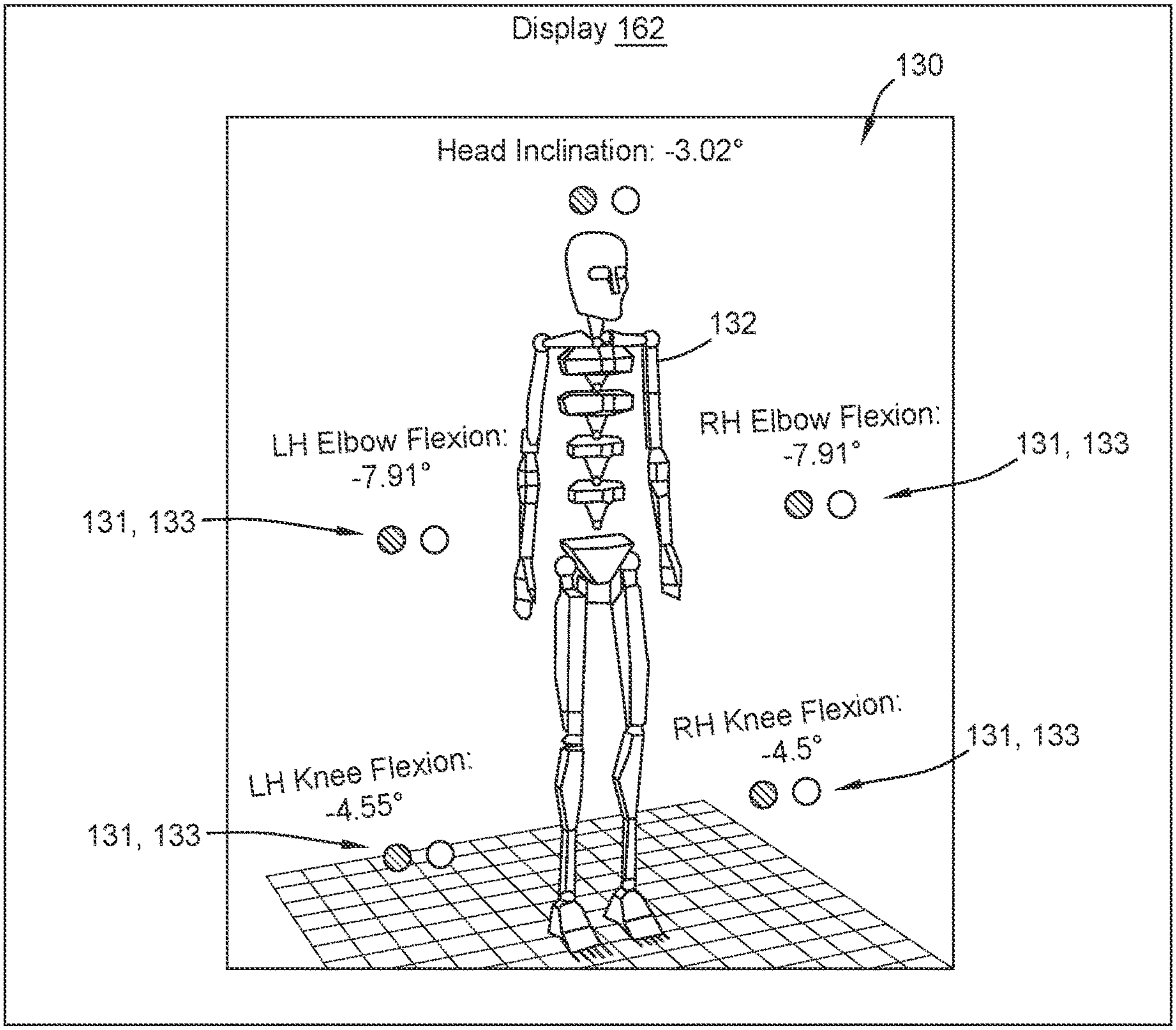
FIG. 2 depicts a rendering of a 3D environment with a user presented on a display.

A plurality of physiological angles 138 and corresponding visual cues 131 can be determined and presented on the display 162 during a simulation. For instance, FIG. 2 depicts a rendering of the 3D environment 130 with the user 132 presented on the display 162. As illustrated, the physiological angles 138 can include a joint angle corresponding to a head inclination, a joint angle corresponding to a left elbow flexion, a joint angle corresponding to a right elbow flexion, a joint angle corresponding to a left knee flexion, and a joint angle corresponding to a right knee flexion. Other physiological angles 138 are possible. Each physiological angle 138 has a corresponding visual cue 131 (in the form respective color indicators 133) that represent whether a given one of the physiological angles 138 are within the acceptable range of a corresponding anthropometric standard associated with the given physiological angle. The plurality of physiological angles 138 and corresponding visual cues 131 can allow an analyst to assess multiple joints for ergonomic sustainability.

In addition to rendering the 3D environment 130 on the display 162, the computing system 110 can output one or more aural cues. For instance, when a physiological angle 138 angle is not within the acceptable range of the anthropometric standard 148, the computing system 110 can output an aural cue indicating that the physiological angle 138 is associated with a potential ergonomic risk. Moreover, aural cues can be output, e.g., to list off the angles of the physiological angles 138. Aural cues can be output to one or more of the output devices, such as speakers.

In another aspect, the computing system 110 can output ergonomic data sets 172 corresponding to ergonomic data captured during the simulation. As one example, one of the ergonomic data sets 172 can include angle ranges as a function of time, with the angle ranges being captured as the user 132 is moved through a range of motion within the 3D environment 130 during a simulation. As another example, one of the ergonomic data sets 172 can correspond the physiological angles 138 relative to the anthropometric standard 148 through the range of motion of the user 132 in the 3D environment 130, and can indicate when a given physiological angle is not within the anthropometric standard 148. The ergonomic data sets 172 can be output and imported into, e.g., an analysis tool 180. The analysis tool 180 can be a separate tool from the ergonomic assessment tool 100 or can be integrated into the ergonomic assessment tool 100. In this regard, in some aspects, the analysis tool 180 can be a component of the computing system 110.

The analysis tool 180 can include an ergonomic report generator 182 that generates (e.g., automatically) an ergonomic report that indicates one or more potential ergonomic risks. The ergonomic report can include information pertaining to all physiological angles 138, can be specific to a single physiological angle 138, or can include information pertaining to only physiological angles 138 associated with a potential ergonomic risk.

Figure 3:
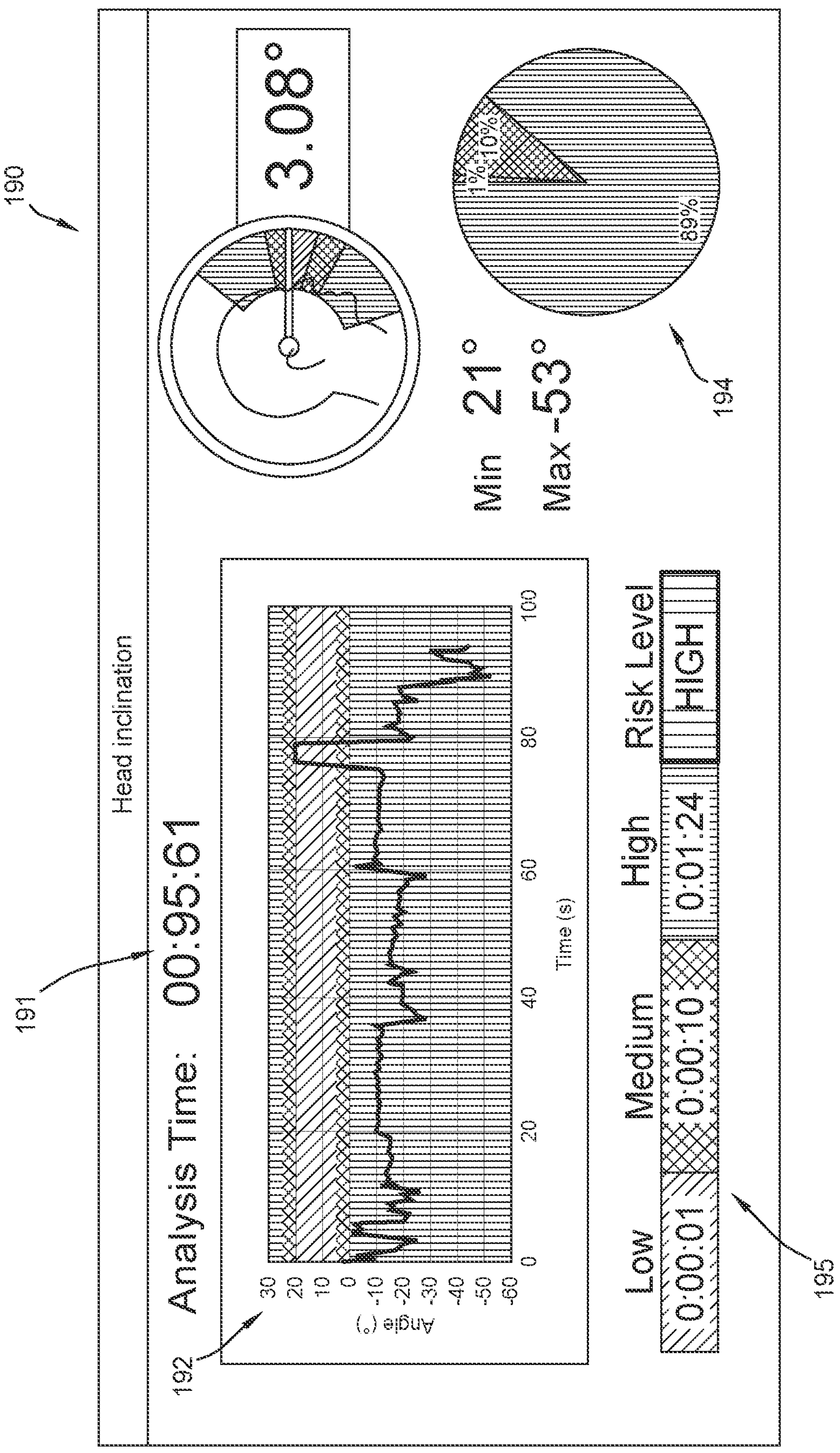
FIG. 3 depicts one example ergonomic report according to aspects of the present disclosure.

FIG. 3 depicts one example ergonomic report 190 that is specific to the head inclination of the user 132 rendered on the display 162 of FIG. 1. As shown, the ergonomic report 190 can include an evaluation time 191, which in this example is approximately ninety-five (95) seconds. The ergonomic report 190 can also depict a range of acceptable head inclination, given the anthropometric standard 148 selected. In this example, an angle of 0° to 25° is an acceptable range of head inclination. Moreover, the ergonomic report 190 can also include a graph 192 that presents the head inclination of the user 132 as a function of time. The ergonomic report 190 can also depict a maximum head inclination angle, which is −53°, and a minimum head inclination angle, which is −21° in this example. Further, the ergonomic report 190 can indicate a potential ergonomic risk by showing a percentage of time during the simulation that the head inclination angle is not within an acceptable range of the anthropometric standard 148. For instance, in the ergonomic report 190, a pie chart 194 is depicted showing that: one percent (1%) of the time the head inclination angle was in a low ergonomic risk state; ten percent (10%) of the time the head inclination angle was in a medium ergonomic risk state, and eighty-nine percent (89%) of the time the head inclination angle was in a high ergonomic risk state. The time the head inclination angle was in each state can also be presented, e.g., in a table 195. Similar ergonomic reports associated with other physiological angles 138 (FIGS. 1 and 2) can be generated as well. Based on such reports, an analyst can assess the ergonomics of a workspace.

In yet another aspect, the computing system 110 can generate workspace change recommendations 174. For instance, in some aspects, the computing system 110 can include an improvement generator 122. The improvement generator 122, when executed, can determine the workspace change recommendations 174 or design changes that can possibly be made to the workspace 134 to improve the ergonomics thereof. The output generator 120 can output the workspace change recommendations 174, e.g., to the display 162 so that the workspace change recommendations 174 can be presented to an analyst. In some example aspects, the improvement generator 122 can analyze the ergonomic data sets 172 or other assessment data collected during the simulation and can determine which components of the workspace 134 affect, or are the root cause of, one or more of the physiological angles 138 not being within the anthropometric standard 148. Such components can be noted and presented to an analyst, e.g., on the display 162.

Figure 4:
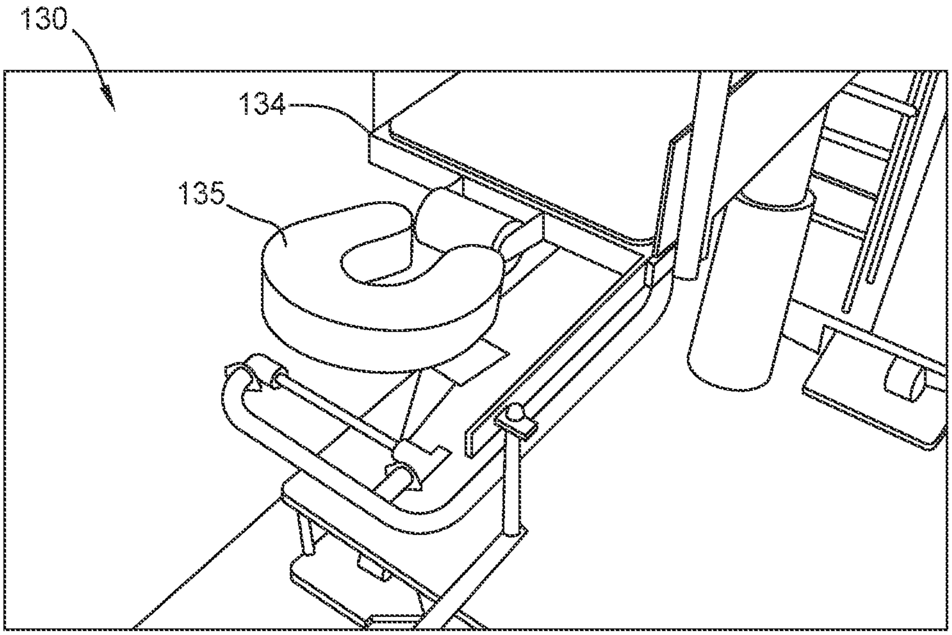
FIGS. 4 and 5 depict renderings of a 3D environment in which a modified component has been incorporated into a simulation.
Figure 5:
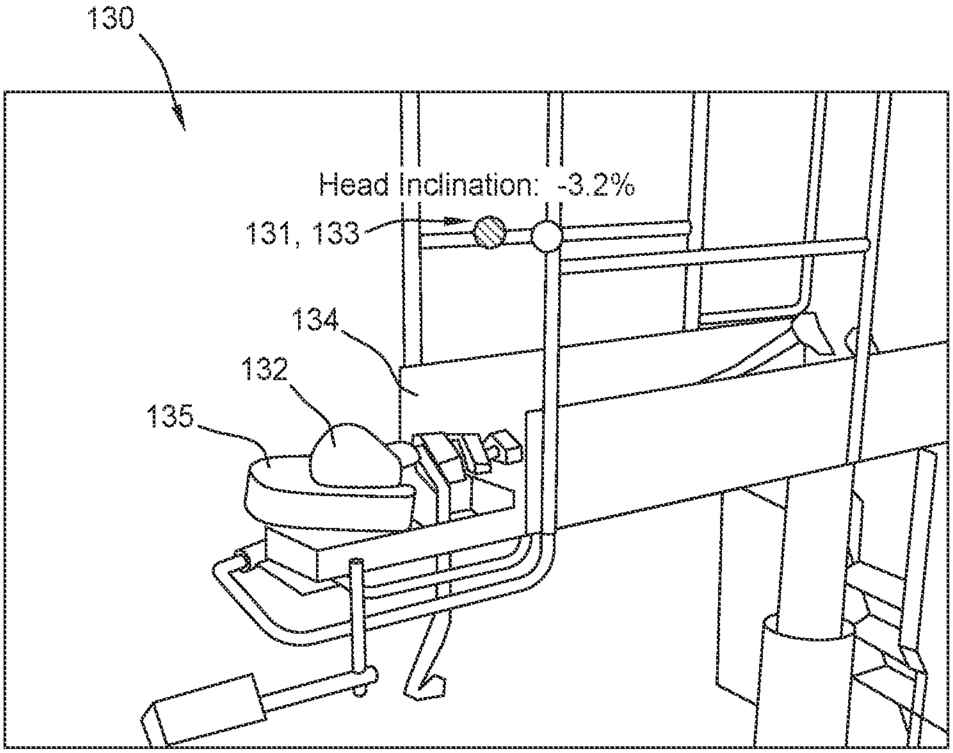

In some further aspects, the workspace 134 can be modifiable in real time, e.g., during a simulation, between simulations, etc. For instance, components of the workspace 134 can be selectable and can be modified, e.g., by way of analyst inputs 150. By way of example, the headrest 136 of the workspace 134 depicted in FIG. 1 has shown to position the head of the user 132 at a head inclination angle of −7.86°, which is not within an acceptable anthropometric standard (e.g., as indicated by color presented by the visual cue 131). Accordingly, a user can select the headrest 136 and can replace the headrest 136 with a modified headrest. FIG. 4 depicts a modified headrest 135 that has replaced the headrest 136 of FIG. 1. The modified headrest 135 is configured as a face cradle that allows the user 132 to place her face within the opening of the cradle with forehead and cheeks resting on the cradle. As shown in FIG. 5, the user 132 can be placed in position relative to the modified headrest 135. The physiological angle 138, or head inclination angle in this example, is now presented as −3.2%, which as indicated by the visual cue 131, is an acceptable angle of inclination for the head according to the anthropometric standard 148. Consequently, the color indicator 133 is the first color (e.g., green), as indicated by the circle containing the hatching. Such a visual cue can allow an analyst to readily appreciate that the head inclination angle meets the anthropometric standard 148.

The ability to modify the workspace 134 in real time during a simulation can allow an analyst to determine possible solutions for addressing potential ergonomic risks in real time. In some aspects, the 3D models input into the computing system 110 can include a library of possible replacement components (e.g., a library of a plurality of potential headrests) for the workspace 134. In this way, an analyst can swap out and quickly determine viable components for the workspace 134. In other aspects, the 3D environment generator 112 can allow for components of the workspace 134 to be modified by changing their dimensions or by "drawing in" a modified component. Accordingly, in response to determining that a physiological angle of the user is not within an acceptable anthropometric standard and represents a potential ergonomic risk, the method implemented by the computing system 110 is configured to modify the workspace 134 within the 3D environment 130 to determine a possible ergonomic solution to the potential ergonomic risk, and the computing system 110 performs a further simulation to determine that the ergonomic solution addresses the potential ergonomic risk, wherein the ergonomic solution is implemented within the physical workspace to eliminate the potential ergonomic risk to the user.

Figure 6:
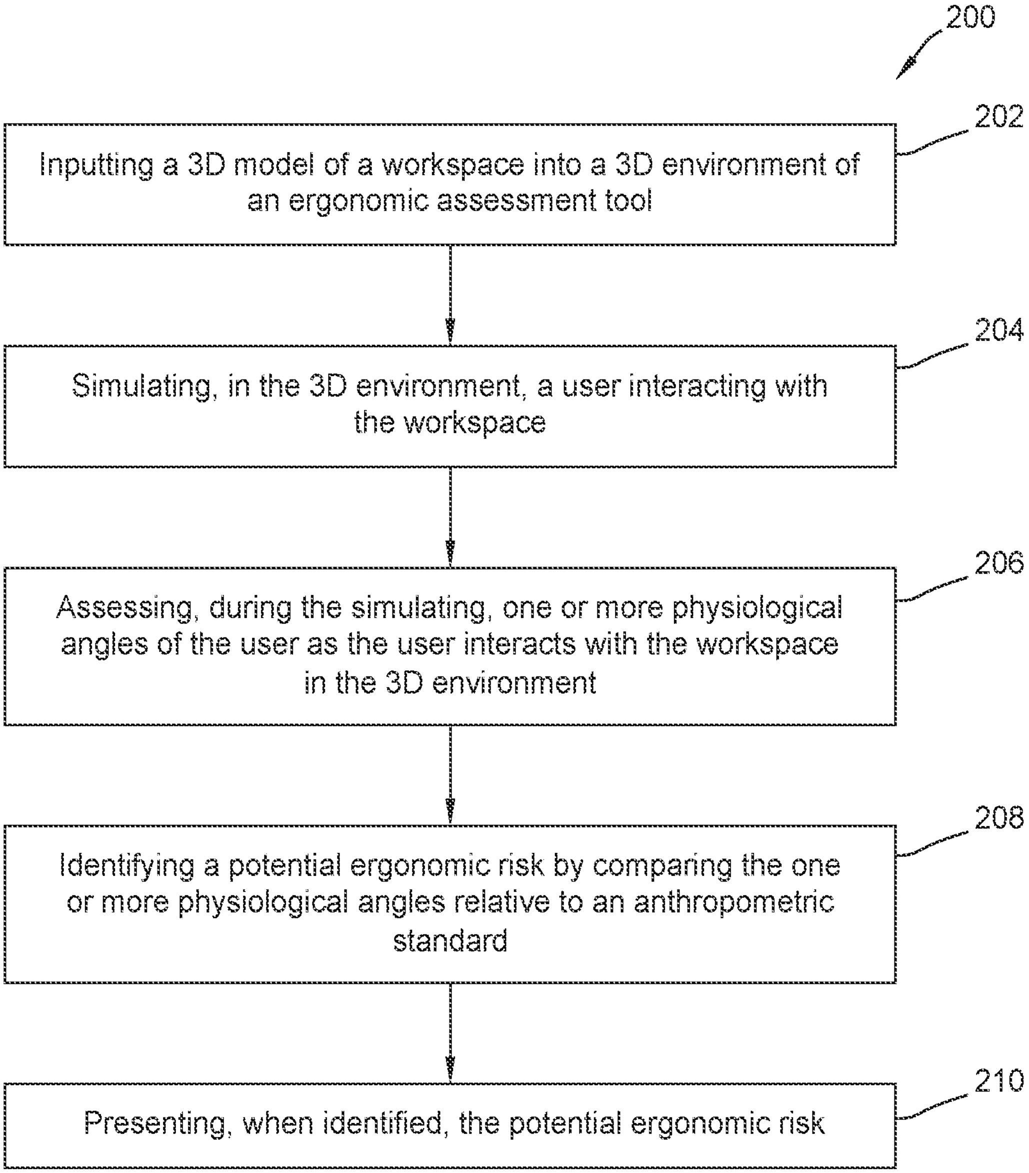
FIG. 6 is a flow diagram of an example method according to aspects of the present disclosure.

FIG. 6 is a flow diagram of a method 200 according to example aspects of the present disclosure.

At 202, the method 200 can include inputting a 3D model of a workspace into a 3D environment of an ergonomic assessment tool. For instance, a 3D model can be input into a computing system of an ergonomic assessment tool. The computing system can include a 3D environment generator configured to generate a 3D environment. The 3D environment generator can generate a 3D environment that includes the workspace, or design desired to be ergonomically analyzed.

At 204, the method 200 can include simulating, in the 3D environment, a user interacting with the workspace. For instance, the 3D environment generator can generate the 3D environment that includes the workspace and a bidpedal motion generator can be used to statically place or otherwise move a user within the 3D environment to interact with the workspace. In some implementations, the method 200 can include acquiring motion data from an actual user performing an actual range of motion, e.g., in a real environment. The range of motion that the user performs to interact with the workspace in the 3D environment can mimic the actual range of motion. Accordingly, the captured motion data can be used by the bidpedal motion generator to move the user about the 3D environment relative to the workspace. In other implementations, a user can be moved about the 3D environment in other suitable manners, such as by an analyst input.

Moreover, in some implementations, the method 200 can include applying, during the simulating, a gravity modifier so as to simulate gravity on the user in the 3D environment. This can enhance the accuracy of the assessment. The gravity applied can be selected to match expected conditions in which the workspace will be utilized. In some implementations, the anthropometric standard can be adjustable in real time during the simulating. For instance, an analyst can adjust the anthropometric standard, e.g., from a first standard to a second standard. This can allow an analyst to assess the ergonomics of a workspace in view of different anthropometric standards.

At 206, the method 200 can include assessing, during the simulating, one or more physiological angles of the user as the user interacts with the workspace in the 3D environment. For instance, the computing system can include an assessment generator that monitors the user's interaction with the workspace during the simulation. In this regard, one or more physiological angles of the user (e.g., joint angles) can be determined as the user interacts with the workspace in the 3D environment. In some implementations, the one or more physiological angles can be presented, on a display during the simulating, adjacent respective joints of the user. For instance, a head inclination angle can be presented on the display adjacent the head or neck area of the user. The one or more physiological angles can be dynamically updated on the display as the user moves through a range of motion. The one or more physiological angles can correspond to joint angles, posture angles, or both, of the user.

In some implementations, the workspace can be modifiable in real time during the simulating. For instance, one or more components of the workspace can be modified or swapped out with other different components in real time, e.g., during a simulation. Such a feature can enable an analyst to determine possible solutions for addressing potential ergonomic risks in real time.

At 208, the method 200 can include identifying a potential ergonomic risk by comparing the one or more physiological angles relative to an anthropometric standard. For instance, when a given physiological angle is determined to fall outside of an acceptable range that corresponds to the given physiological angle, a potential ergonomic risk associated with the given physiological angle can be identified.

In some implementations, the method 200 can include generating a workspace change recommendation for the workspace based at least in part on the potential ergonomic risk that is identified. In some aspects, the computing system can determine the workspace change recommendations or design changes that can possibly be made to the workspace to improve the ergonomics thereof, based at least in part on the identified potential ergonomic risks. The computing system can determine which components of the workspace affect, or are the root cause of, one or more of the physiological angles not being within the anthropometric standard. Such components can be noted and presented to an analyst in the form of a workspace change recommendation.

At 210, the method 200 can include presenting, when identified, the potential ergonomic risk, e.g., to an analyst. For instance, an identified potential ergonomic risk can be presented to an analyst on a display, through speakers, via reports, some combination thereof, etc.

In some implementations, for example, presenting the potential ergonomic risk comprises presenting, on a display in real time, a visual cue indicating that one of the physiological angles is not within an acceptable range of the anthropometric standard. The visual cue indicating that the physiological angle is not within the acceptable range of the anthropometric standard can be presented as a color indicator positioned adjacent the physiological angle of the user on the display. The color indicator can be changed from a first color (e.g., green) to a second color (e.g., red) when the physiological angle is not within the acceptable range of the anthropometric standard. This can make a potential ergonomic risk readily apparent to an analyst.

In some implementations, presenting the potential ergonomic risk can include exporting an ergonomic data sheet that corresponds the one or more physiological angles relative to the anthropometric standard through a range of motion of the user. As one example, the ergonomic data sheet can be exported to an ergonomic report generator that generates an ergonomic report that indicates the potential ergonomic risk to the user as a number of instances per unit of time that at least one of the one or more first physiological angles of the one or more physiological angles is not within an acceptable range of the anthropometric standard. As another example, the ergonomic data sheet can be exported to an ergonomic report generator that generates an ergonomic report that indicates the potential ergonomic risk to the user as a percentage of time during the simulation that at least one of the one or more first physiological angles of the one or more physiological angles is not within an acceptable range of the anthropometric standard.

Figure 7:
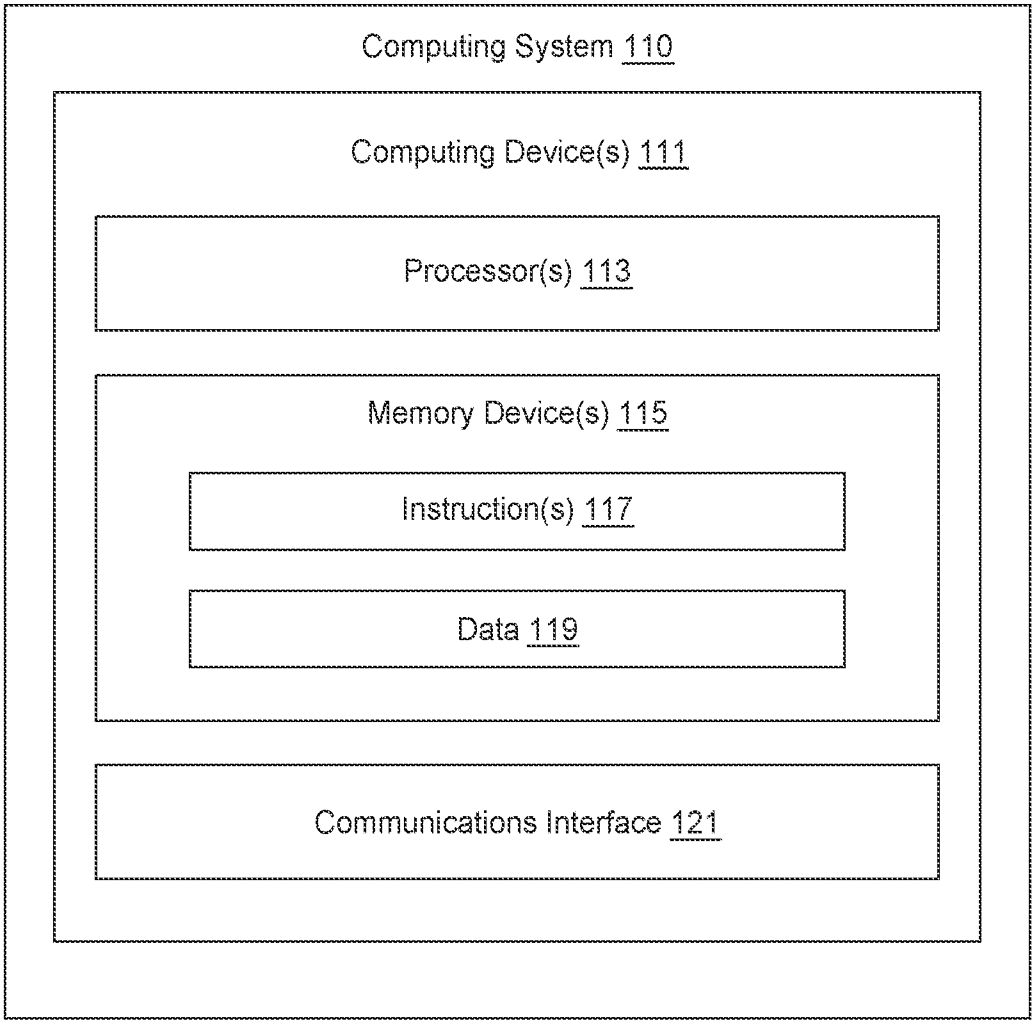
FIG. 7 is a block diagram of a computing system for implementing one or more aspects of the present disclosure.

FIG. 7 is a block diagram depicting the architecture of the computing system 110 of FIG. 1.

As shown in FIG. 7, the computing system 110 can include one or more computing device(s) 111. The one or more computing device(s) 111 can include one or more processor(s) 113 and one or more memory device(s) 115. The one or more processor(s) 113 can include any suitable processing device, such as a microprocessor, microcontroller, integrated circuit, logic device, or other suitable processing device. The one or more memory device(s) 115 can include one or more computer-readable medium, including, but not limited to, non-transitory computer-readable medium, RAM, ROM, hard drives, flash drives, and other memory devices.

The one or more memory device(s) 115 can store information accessible by the one or more processor(s) 113, including computer-readable instructions 117 that can be executed by the one or more processor(s) 113. The instructions 117 can be any set of instructions that when executed by the one or more processor(s) 113, cause the one or more processor(s) 113 to perform operations. The instructions 117 can be software written in any suitable programming language or can be implemented in hardware.

The memory device(s) 115 can further store data 119 that can be accessed by the processors 113. For example, the data 119 can include any of the data noted herein. The data 119 can include one or more table(s), function(s), algorithm(s), model(s), equation(s), etc. according to example aspects of the present disclosure.

The one or more computing device(s) 111 can also include a communication interface 121 used to communicate, for example, with the other components of the ergonomic assessment tool 100. The communication interface 121 can include any suitable components for interfacing with one or more network(s), including for example, transmitters, receivers, ports, controllers, antennas, or other suitable components.

In the current disclosure, reference is made to various aspects. However, it should be understood that the present disclosure is not limited to specific described aspects. Instead, any combination of the following features and elements, whether related to different aspects or not, is contemplated to implement and practice the teachings provided herein. Additionally, when elements of the aspects are described in the form of "at least one of A and B," it will be understood that aspects including element A exclusively, including element B exclusively, and including element A and B are each contemplated. Furthermore, although some aspects may achieve advantages over other possible solutions and/or over the prior art, whether or not a particular advantage is achieved by a given aspect is not limiting of the present disclosure. Thus, the aspects, features, aspects and advantages disclosed herein are merely illustrative and are not considered elements or limitations of the appended claims except where explicitly recited in a claim(s).

As will be appreciated by one skilled in the art, aspects described herein may be embodied as a system, method or computer program product. Accordingly, aspects may take the form of an entirely hardware aspect, an entirely software aspect (including firmware, resident software, micro-code, etc.) or an aspect combining software and hardware aspects that may all generally be referred to herein as a "circuit," "module" or "system." Furthermore, aspects described herein may take the form of a computer program product embodied in one or more computer readable storage medium(s) having computer readable program code embodied thereon.

Program code embodied on a computer readable storage medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations and/or block diagrams of methods, apparatuses (systems), and computer program products according to aspects of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block(s) of the flowchart illustrations and/or block diagrams.

These computer program instructions may also be stored in a computer readable medium that can direct a computer, other programmable data processing apparatus, or other device to function in a particular manner, such that the instructions stored in the computer readable medium produce an article of manufacture including instructions which implement the function/act specified in the block(s) of the flowchart illustrations and/or block diagrams.

The computer program instructions may also be loaded onto a computer, other programmable data processing apparatus, or other device to cause a series of operational steps to be performed on the computer, other programmable apparatus or other device to produce a computer implemented process such that the instructions which execute on the computer, other programmable data processing apparatus, or other device provide processes for implementing the functions/acts specified in the block(s) of the flowchart illustrations and/or block diagrams.

The flowchart illustrations and block diagrams in the Figures illustrate the architecture, functionality, and operation of possible implementations of systems, methods, and computer program products according to various aspects of the present disclosure. In this regard, each block in the flowchart illustrations or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order or out of order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

While the foregoing is directed to aspects of the present disclosure, other and further aspects of the disclosure may be devised without departing from the basic scope thereof, and the scope thereof is determined by the claims that follow.

What is claimed is:

1. A method, comprising:

inputting a three-dimensional (3D) model of a workspace into a 3D environment of an ergonomic assessment tool;

receiving physics-based gravity data and a selection of a gravitational force of a plurality of gravitational forces, wherein the physics-based gravity data comprises a plurality of data sets, each data set of the plurality of data sets comprising a plurality of scripts executable to simulate the effects of gravity on the angle of inclination; and repeatedly and automatically, until a potential ergonomic risk is below a predetermined threshold:

simulating, in the 3D environment, a user interacting with the workspace;

applying, during the simulating, a gravity modifier so as to simulate gravity on the user in the 3D environment based on the physics-based gravity data, wherein the gravity modifier comprises the selected gravitational force and is based at least in part on at least one data set of the plurality of data sets, the at least one data set corresponding to at least one of an altitude or latitude of the workspace;

assessing, during the simulating, one or more physiological angles of the user as the user interacts with the workspace in the 3D environment, wherein the one or more physiological angles are based on the simulated gravity on the user in the 3D environment and comprise an angle of inclination of the user with respect to a work surface of the workspace due to the simulated gravity;

identifying the potential ergonomic risk by comparing the angle of inclination relative to an anthropometric standard;

presenting, when identified, the potential ergonomic risk; and modifying the 3D model of the workspace based on the potential ergonomic risk.

2. The method of claim 1, further comprising modifying the 3D model during the simulating by simulating at least one of the following for a component of the workspace selected from a library of components: replacement, resizing, or repositioning.

3. The method of claim 1, wherein presenting the potential ergonomic risk comprises presenting, on a display in real time, a visual cue indicating that a first physiological angle of the one or more physiological angles is not within an acceptable range of the anthropometric standard.

4. The method of claim 3, wherein the visual cue indicating that the first physiological angle is not within the acceptable range of the anthropometric standard is presented as a color indicator positioned adjacent the first physiological angle of the user on the display, and wherein the color indicator changes from a first color to a second color when the first physiological angle is not within the acceptable range of the anthropometric standard.

5. The method of claim 1, further comprising:

presenting, on a display during the simulating, the one or more physiological angles, wherein the one or more physiological angles are presented adjacent respective joints of the user.

6. The method of claim 5, wherein the one or more physiological angles dynamically update on the display as the user moves through a range of motion.

7. The method of claim 1, further comprising presenting the potential ergonomic risk during the simulating.

8. The method of claim 1, wherein the anthropometric standard is adjustable in real time during the simulating.

9. The method of claim 1, wherein presenting the potential ergonomic risk comprises exporting an ergonomic data sheet that corresponds the one or more physiological angles relative to the anthropometric standard through a range of motion of the user.

10. The method of claim 9, wherein the ergonomic data sheet is exported to an ergonomic report generator that generates an ergonomic report that indicates the potential ergonomic risk to the user as a number of instances per unit of time that at least one of the one or more physiological angles of the one or more physiological angles is not within an acceptable range of the anthropometric standard.

11. The method of claim 9, wherein the ergonomic data sheet is exported to an ergonomic report generator that generates an ergonomic report that indicates the potential ergonomic risk to the user as a percentage of time during the simulating that at least one of the one or more first physiological angles of the one or more physiological angles is not within an acceptable range of the anthropometric standard.

12. The method of claim 1, further comprising:

acquiring motion data from an actual user performing an actual range of motion, and wherein a range of motion that the user performs to interact with the workspace in the 3D environment mimics the actual range of motion.

13. The method of claim 1, wherein the workspace is modified in real time.

14. The method of claim 1, further comprising:

generating a workspace change recommendation for the workspace based at least in part on the potential ergonomic risk that is identified.

15. An ergonomic assessment tool, comprising:

one or more processors;

one or more memory devices storing a program, which, when executed by any combination of the one or more processors, causes the one or more processors to perform an operation, the operation comprising:

inputting a three-dimensional (3D) model of a workspace into a 3D environment of the ergonomic assessment tool;

receiving physics-based gravity data and a selection of a gravitational force of a plurality of gravitational forces, wherein the physics-based gravity data comprises a plurality of data sets, each data set of the plurality of data sets comprising a plurality of scripts executable to simulate the effects of gravity on the angle of inclination; and repeatedly and automatically, until a potential ergonomic risk is below a predetermined threshold:

simulating, in the 3D environment, a user interacting with the workspace;

applying, during the simulating, a gravity modifier so as to simulate gravity on the user in the 3D environment based on the physics-based gravity data, wherein the gravity modifier comprises the selected gravitational force and is based at least in part on at least one data set of the plurality of data sets, the at least one data set corresponding to at least one of an altitude or latitude of the workspace;

assessing, during the simulating, one or more physiological angles of the user as the user interacts with the workspace in the 3D environment, wherein the one or more physiological angles are based on the simulated gravity on the user in the 3D environment and comprise an angle of inclination of the user with respect to a work surface of the workspace due to the simulated gravity;

identifying the potential ergonomic risk by comparing the angle of inclination relative to an anthropometric standard;

causing, when identified, the potential ergonomic risk to be presented; and modifying the 3D model of the workspace based on the potential ergonomic risk.

16. The ergonomic assessment tool of claim 15, wherein, in causing the potential ergonomic risk to be presented, when identified, the operation comprises:

presenting, on a display in real time, a visual cue indicating that a first physiological angle of the one or more physiological angles is not within an acceptable range of the anthropometric standard.

17. The ergonomic assessment tool of claim 15, wherein the operation further comprises:

presenting, on a display during the simulating, wherein the one or more physiological angles, the one or more physiological angles are presented adjacent respective joints of the user, and wherein the one or more physiological angles dynamically update on the display as the user moves through a range of motion.

18. The ergonomic assessment tool of claim 15, wherein the workspace is modifiable in real time during the simulating.

19. A non-transitory, computer readable medium comprising instructions that, when executed by one or more processors, cause the one or more processors to perform an operation, the operation comprising:

inputting a three-dimensional (3D) model of a workspace into a 3D environment of an ergonomic assessment tool;

receiving physics-based gravity data and a selection of a gravitational force of a plurality of gravitational forces, wherein the physics-based gravity data comprises a plurality of data sets, each data set of the plurality of data sets comprising a plurality of scripts executable to simulate the effects of gravity on the angle of inclination; and repeatedly and automatically, until a potential ergonomic risk is below a predetermined threshold:

simulating, in the 3D environment, a user interacting with the workspace;

applying, during the simulating, a gravity modifier so as to simulate gravity on the user in the 3D environment based on the physics-based gravity data, wherein the gravity modifier comprises the selected gravitational force and is based at least in part on at least one data set of the plurality of data sets, the at least one data set corresponding to at least one of an altitude or latitude of the workspace;

assessing, during the simulating, one or more physiological angles of the user as the user interacts with the workspace in the 3D environment, wherein the one or more physiological angles are based on the simulated gravity on the user in the 3D environment and comprise an angle of inclination of the user with respect to a work surface of the workspace due to the simulated gravity;

identifying the potential ergonomic risk by comparing the angle of inclination relative to an anthropometric standard;

causing, when identified, the potential ergonomic risk to be presented; and modifying the 3D model of the workspace based on the potential ergonomic risk.

* * * * *